United States Patent [19]
Langer et al.

[11] Patent Number: 6,004,295
[45] Date of Patent: Dec. 21, 1999

[54] CATHETERS

[75] Inventors: Anatoly Langer; Duncan John Stewart, both of Toronto, Canada

[73] Assignee: AN-GO-GEN Inc., Toronto, Canada

[21] Appl. No.: 09/104,991

[22] Filed: Jun. 26, 1998

Related U.S. Application Data

[60] Provisional application No. 60/050,805, Jun. 26, 1997.

[51] Int. Cl.$^6$ .......................... A61M 5/178; A61M 5/00; A61M 5/315; A61M 25/01
[52] U.S. Cl. .......................... 604/164; 604/181; 604/185; 604/218; 604/528
[58] Field of Search ..................................... 604/115, 117, 604/118, 121, 125, 132, 158, 162, 164, 181, 185, 187, 214, 216, 217, 218, 264, 523, 528; 600/432, 433, 434, 435

[56] References Cited

U.S. PATENT DOCUMENTS

| | | |
|---|---|---|
| 2,923,295 | 2/1960 | Guerriero . |
| 3,380,448 | 4/1968 | Sadove et al. . |
| 3,508,548 | 4/1970 | Hochstrasser et al. . |
| 4,136,695 | 1/1979 | Dafoe . |
| 4,222,380 | 9/1980 | Terayama . |
| 4,728,322 | 3/1988 | Walker et al. ............................ 604/165 |
| 4,850,978 | 7/1989 | Dudar et al. .............................. 604/201 |
| 5,207,647 | 5/1993 | Phelps . |
| 5,419,777 | 5/1995 | Hofling . |
| 5,470,318 | 11/1995 | Griffith, III et al. ..................... 604/161 |
| 5,538,504 | 7/1996 | Linden et al. . |
| 5,674,205 | 10/1997 | Pasricha et al. ......................... 604/232 |
| 5,681,278 | 10/1997 | Igo et al. . |
| 5,693,029 | 12/1997 | Leonhardt . |
| 5,704,925 | 1/1998 | Otten et al. .............................. 604/272 |
| 5,775,327 | 7/1998 | Randolph et al. ....................... 128/642 |
| 5,797,899 | 8/1998 | Tilton, Jr. ...................................... 606/1 |
| 5,827,236 | 10/1998 | Takahaski ................................ 604/240 |

FOREIGN PATENT DOCUMENTS

| | | |
|---|---|---|
| 2146989 | 4/1994 | Canada . |
| 2220689 | 11/1996 | Canada . |
| 2222162 | 12/1996 | Canada . |
| 2223954 | 12/1996 | Canada . |
| 2229940 | 3/1997 | Canada . |
| 0 608 985 A1 | 8/1994 | European Pat. Off. . |
| WO 92/20400 | 11/1992 | Japan ..................................... 604/187 |
| WO 94/12226 | 6/1994 | WIPO . |
| WO 95/26776 | 10/1995 | WIPO . |

*Primary Examiner*—Ronald K. Stright, Jr.
*Assistant Examiner*—Patricia M. Bianco
*Attorney, Agent, or Firm*—Sixeby, Friedman, Leedom & Ferguson, P.C.; Daniel W. Sixeby; Jeffrey L. Costellia

[57] ABSTRACT

A catheter assembly especially adapted for injecting therapeutic liquids such as DNA solutions to a patient's myocardium comprises an elongated guiding catheter for insertion through a patient's artery to the vicinity of the myocardium, a reservoir for therapeutic liquid at the distal end of the guiding catheter, one or more injection needles protruding from the distal end of the guiding catheter and in fluid communication with the reservoir, the extent of needle protrusion being appropriate for penetration of but not passage through the myocardial wall, and an operating device for delivering a predetermined quantity of therapeutic liquid from the reservoir through the needles.

13 Claims, 5 Drawing Sheets

CATHETERS

This application is a continuation of U.S. Provisional Patent Application No. 60/050,805, filed Jun. 26, 1997 and now abandoned.

FIELD OF THE INVENTION

This invention relates to delivery systems for drugs or biologicals, and more specifically to catheter systems for the delivery of drugs or biologicals to specific internal organs of the body, in precise, predetermined manner.

BACKGROUND OF THE INTENTION

Catheters are, essentially, elongated flexible narrow-bore tubes used to gain access to body organs from the exterior of the body, through the body's natural ducts. They may be inserted, for example, through a patient's urethra to enter the bladder, to drain fluids therefrom or to deliver fluids thereto. They may be inserted into a major artery, and fed through the artery a considerable distance, e.g. to the vicinity of the heart. Instead of being used for the delivery or collection of fluids, they may be equipped with medical devices so that a specific medical procedure can be performed at a particular location of the artery, such as an angioplasty to relieve an occluded or partially occluded artery.

Accordingly, catheters have a number of very demanding technical criteria to meet. They must be flexible enough and thin enough to accommodate the contours of the body duct, without causing internal damage. They must provide reliable fluid communication over substantial distances. They must exhibit a high degree of biocompatibility. Their distal ends must be equipped with appropriate apparatus to perform their intended function. Commonly, such apparatus must be arranged so as to be operable from outside the patient's body, after insertion of the catheter to its correct location.

There are instances where, for critical therapeutic purposes, it is necessary to inject a patient's myocardium with a therapeutic fluid, such as a DNA solution, in very small amounts and at a precise location. The myocardium is the middle, cardiac muscle portion of the heart wall, surrounding the heart chambers. It is the thickest part of the heart wall, having a maximum thickness, in the ventricle walls, of about 2.5 cm. Blood vessels permeate the myocardium. The capillary beds therein are so extensive that more oxygen is released in the myocardium by the circulating blood than in any other organ of the body. Localized treatment of the myocardium to treat muscular damage thereto, e.g. with therapeutic substances, is sometimes needed. Very precise control over the location and delivery of such therapeutic substances is accordingly necessary. Very small amounts of very expensive therapeutic substances such as up to 0.05 ml of DNA solution are often required to be delivered, with precise control over location and quantity.

It is an object of the present invention to provide a novel catheter for fluid delivery to internal organs of a mammalian body.

It is a further object of the invention to provide a catheter specifically adapted for delivering fluids to the myocardium.

SUMMARY OF THE INVENTION

The present invention provides a novel form of fluid delivery catheter assembly capable of delivering therapeutic fluids to a precisely controlled, predetermined location of an internal organ of the body such as the myocardium. The fluid delivery catheter assembly comprises (a) an elongated flexible biocompatible tube effectively constituting a guiding catheter; (b) one or more injection needles at the distal end of the guiding catheter, the needles carefully arranged so that they can be inserted into, but will not protrude through, an internal organ wall such as a patient's myocardium; and (c) a reservoir adapted to contain therapeutic fluid, carried by the catheter and in fluid communication with the injection needles. An operating means is provided which can be operated exteriorly of the body being treated, when the catheter is in place, to deliver a predetermined quantity of fluid from the reservoir to and through the needles. The catheter assembly is adapted for insertion through a vascular structure of the body, to an internal organ. In the case of treatment of the myocardium, the catheter assembly may be inserted through either of the right or left femoral vein or right or left jugular vein into the right ventricle, to effect injection into the ventricular septum. Alternatively, the catheter assembly can be deployed in the left ventricle, with approach through either right or left femoral artery or right or left brachial artery, and injection in either ventricular septum or anterior or inferior or posterolateral left ventricular free wall. The shape of the distal end portion of the catheter assembly can be arranged to meet the manner of intended approach and injection.

BRIEF REFERENCE TO THE DRAWINGS

DESCRIPTION OF THE PREFERRED EMBODIMENTS

One preferred form of reservoir for use in the fluid delivery catheter of the present invention is a cartridge, removably and slidably mounted in the distal end portion of the guiding catheter. Such a cartridge is suitably cylindrical, so as to fit slidably inside the distal end portion of the guiding catheter, and to be moveable towards and away from the distal end of the guiding catheter. It is thus a custom made unit, sized so as to contain from 0.05–10 ml of fluid. Most preferably, its proximal end is in the form of reciprocal plunger, adapted to move in increments towards the distal end of the cartridge.

The distal end of the cartridge is suitably equipped with a mounting plate carrying one or more needles which protrude distally therefrom a suitable distance for effective fluid delivery as required, namely 1–8 mm. The needles have central bores which communicate with the interior of the cartridge, and one or more (up to about 10) outlet openings in the length of their extent beyond the distal end of the cartridge. Thus the outlet openings may be disposed radially or axially of the needle. In such an arrangement, each incremental movement of the plunger toward the distal end of the cartridge can cause the expulsion through the injection needle(s) of a predefined aliquot of liquid, e.g. of volume 0.05–0.5 ml, from the cartridge.

Other preferred embodiments of the invention have the reservoir in the form of a chamber in an interior injection catheter, in fluid communication with the injection needle (s), the injection catheter being adapted to be received within the guiding catheter. Biological fluid may be expelled from the chamber through the injection needle(s), in known, predetermined amounts, by application of pressure to the fluid in the chamber. This can be accomplished, for example, by compressing the chamber by application of external pressure to resilient walls of the chamber, or by direct application of fluid pressure to the liquid in the chamber from the proximal end of the catheter assembly.

Some preferred embodiments of the invention include a guide wire extending along the inside length of the guiding catheter and through the reservoir and needle. This guide wire is moveable lengthwise relative to the guiding catheter. It can be arranged to protrude distally beyond the distal end of the guiding catheter. Such a guide wire, being of smaller diameter, is more flexible and capable of more intricate shaping than the guiding catheter, e.g. into sharper curved shapes, necessary to allow contact with portions of the myocardial wall which present access difficulties. When, for example, access to the myocardial wall of the left ventricular chamber via the aortic valve is required, the catheter must negotiate fairly sharp curves in the artery for access. A flexible, shape assuming guide wire as the leading element of the catheter of the present invention in such an arrangement is advantageous in such applications. When the guide wire has been placed in position against the myocardial wall, the guiding catheter and associated reservoir can be moved along it, ready for injection of drug. The guide wire suitably protrudes also from the proximal end of the guiding catheter, so that the operator can use both the guide wire and the guiding catheter to insert and place the catheter in the correct position. In some embodiments, the guide wire can also act as a stiffener for the guiding catheter. Suitable guide wires are available on the market.

Some preferred embodiments of the invention suitably includes an injection catheter disposed inside the biocompatible tube and extending along the length thereof. When the embodiment includes a cartridge with a reciprocal plunger, the injection catheter may have its distal end connected to the plunger comprising the proximal end of the cartridge, so that the injection catheter effectively forms part of the operating means. It is connected at or near its proximal end to a fluid pressure injector so that the plunger can be moved hydraulically by means of a syringe or similar device, to deliver fluid from the cartridge to the needles.

The biocompatible tube comprising the guiding catheter is suitably made of polyethylene, or other suitable artificial plastic substance with appropriate flexibility and biocompatibility such as nylon, polypropylene, etc. Typically, it has a length between 1 meter and 2 meters, and a diameter between 4 F and 8 F (1.5–3.0 mm). It may have a central lumen to accommodate an injection catheter and a distal end portion for containment and deployment of drug delivery components. The distal end portion of this guiding catheter, of length approximately 1–15 cm, may have a variety of different shapes, to facilitate reaching a particular myocardial wall for which it is employed. The individual shapes are largely determined by the approach which the operator intends to take, to the treatment of the internal organ such as the myocardium, and the disposition of the portion of the organ which it is intended to penetrate and treat. Thus the distal end portion thereof may comprise a straight catheter, or a curved portion with the arc of curvature varying between 30° and 180°. It can be of S-shape with varying degrees of arc in the proximal portion and the distal portion of this end portion. The distal endmost portion can be U-shaped, over its 0.5–2.0 cm distal tip length, with varying degrees of the arc. It can have more than one angularly disposed portion, with a first, proximal end angulation in the range 90–160° and the second, distal end angulation portion being in the range 100–170°. The distal tip of the guiding catheter may be straight or angular with respect to its length, with angles varying between 90° and 160°.

A special type of guide wire for use in the present invention, in a preferred embodiment thereof, includes a screw attached to its distal end, adapted to protrude beyond the distal end of the cartridge and the guiding catheter so as to be available for direct contact and attachment to the myocardial wall. This allows for accurate placement of the catheter on the myocardial wall, and retention in place of the apparatus on the preselected portion of the myocardial wall while the injection of fluid from the cartridge into the myocardium takes place.

A feature of the preferred catheter assemblies of the invention is the limitation of the protrusion of the injection needles to not more than about 2.5 cm, most preferably not more than about 8 mm, beyond the distal end thereof, even when fully extended. This ensures proper penetration into the thickness of the myocardium for treatment thereof, e.g. to repair damaged vessels, without risk of full penetration through the entire thickness of the myocardium. Means for monitoring the position and penetration of the injection needles may be included on the assembly, such as tip electrodes on the needles and reference electrodes on the body of the assembly which, with appropriate, standard electrical circuitry will give the operator an audible or visible signal when contact and/or appropriate penetration of the treatment site has been achieved. Parts are also (or alternatively) rendered radiation opaque so that the operation of the catheter assemblies according to the invention can be monitored on screen as it is conducted.

Specific Description of the Most Preferred Embodiments

Figure 1:
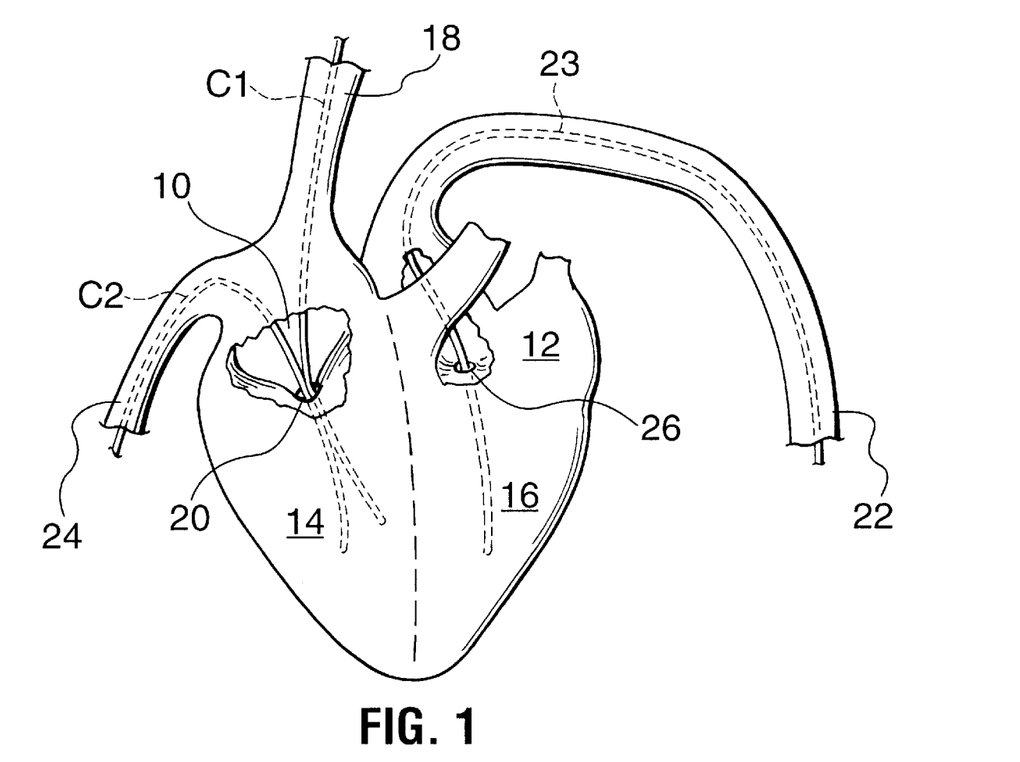
FIG. 1 is a diagrammatic four-chamber view of a human heart, and illustrating diagrammatically and in broken lines three alternative ways for insertion of a catheter according to the invention.

FIG. 1 of the accompanying drawings diagrammatically illustrates the human heart, and three alternative ways in which catheters of the present invention may be inserted, to permit injections into the myocardium at different general locations. The heart has four chambers, namely a right atrium 10, a left atrium 12, a right ventricle 14 and a left ventricle 16. The ventricles are capable of a pumping action, and are lined with a muscular wall, the myocardium, which creates the pumping action. Treatment of the myocardium to improve or repair its function is sometimes necessary. The present invention provides catheters suitable for this purpose:

The superior vena cava 18 is a main body vein, communicating with the right atrium 10, which in turn communicates via the tricuspid valve 20 with the right ventricle 14. The inferior vena cava 24 is another main body vein communicating with the right atrium 10. Accordingly, a catheter according to the invention can be inserted into the right ventricle 14 for treatment of its myocardial wall either via superior vena cava 18 and tricuspid valve 20, as indicated by broken line C1. Alternatively, it can be inserted through the inferior vena cava 24, right atrium 10 and tricuspid valve 20, into right ventricle 14, as indicated by broken line C2. The left ventricle 16 is similarly accessible through femoral artery 22, left atrium 12 and aortic valve 26 as indicated by broken line 23.

Figure 2:
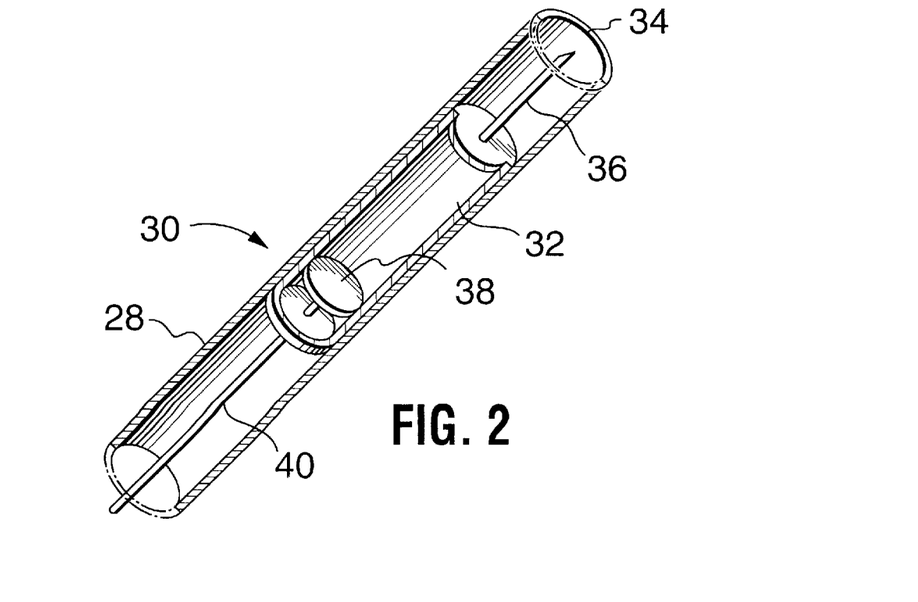
FIG. 2 is a detail diagrammatic view of the distal end portion of a catheter according to a specific preferred embodiment of the invention.
Figure 3:
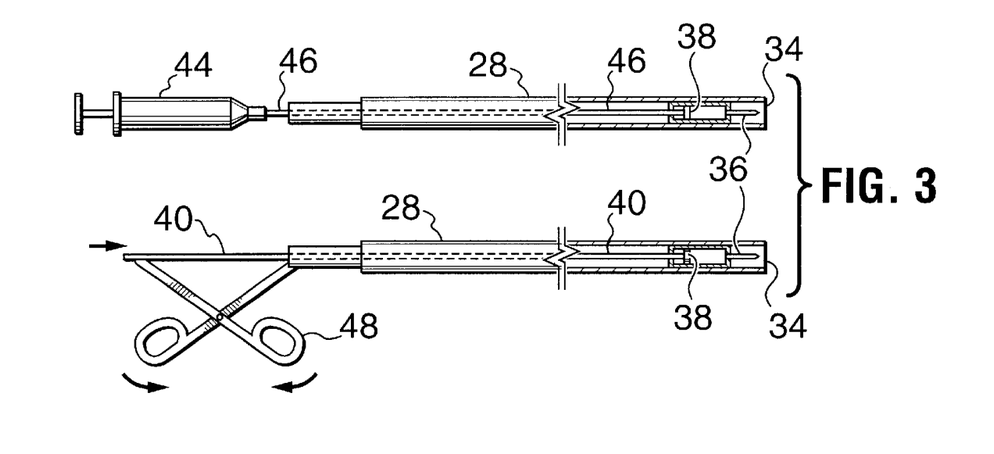
FIG. 3 is a general diagrammatic view of the catheter of FIG. 2, in two alternative forms thereof.

FIG. 2 of the accompanying drawings shows diagrammatically the distal end portion of a catheter 28, according to a preferred embodiment of the invention. Its distal end portion 30 contains a reservoir 32 in the form of a cartridge slidable within the distal end 30 of the catheter 28. Protruding from the end of the cartridge 32 to the distal end 34 of the catheter is a needle 36 in communication with the interior of the cartridge 24. Within the cartridge 32 is a plunger 38 which can move up and down within the cartridge 32 and closely engages the interior walls of the cartridge 32 in a slidable manner. As shown in FIG. 3, the plunger 38 may be mounted on an operating wire 40, or in the alternative with a conduit catheter 46, either of which extends through the length of the catheter 28 to its proximal end, where it is operatively associated with a mechanical device or hydraulic device respectively, adapted to move the cartridge 32 towards the distal end 34 of the catheter 28 and, at the termination of that movement as described below, to move the plunger 38 within the cartridge 32 towards the distal end 34 of the catheter 28, to push the contents of the cartridge 32 into and through the needle 36.

Thus referring to FIG. 3, the complete catheter 28 has, at its proximal end, one of two alternative operating mechanisms. The first is a hydraulic system where the proximal end of the catheter has a source of hydraulic pressure in the form of a hydraulic syringe 44 supplying hydraulic fluid to a conduit catheter 46 which extends to engage the plunger 38 within the cartridge 32. The second is a mechanical, wire activated system in which a scissor-type assembly 48 (or similar device such as a "loop and ring) is attached to one end of operating wire 40, to move it up on mechanical closure of the scissor handles 48 to move the plunger 38 attached to the distal end of the wire 40. The first portion of such movement, when the distal end 34 of the catheter is in contact with the wall of the body organ at the required position, serves to move the cartridge 32 relative to the catheter 28 towards the distal end 34 of the catheter, and to cause penetration of the needle 36 into the body organ walls such as the myocardium, to an extent limited by the length of the needle 36. Once the needle 36 has achieved full penetration, further movement of the plunger 38 takes place within the cartridge 32, and relative thereto, to expel the liquid contents from the cartridge through the needle 36 into the penetrated body wall.

Figure 4A:
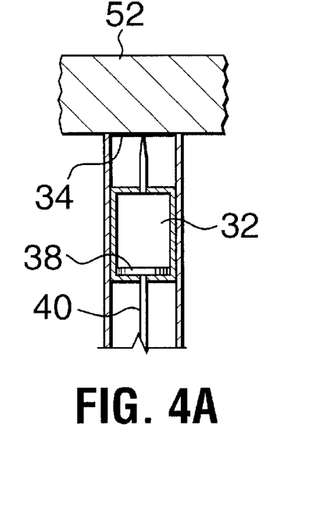
FIGS. 4A, 4B and 4C comprise three sequential diagrammatic views of the distal end of the catheter of FIGS. 2 and 3, showing different stages of the operation thereof.
Figure 4B:
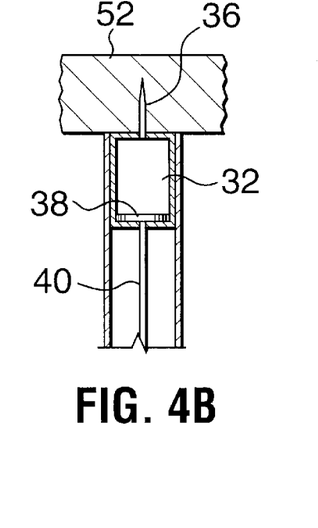
Figure 4C:
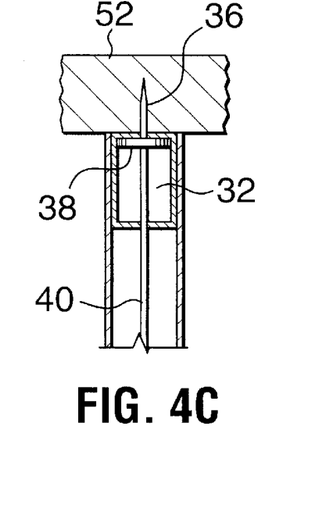

This is further diagrammatically illustrated in FIG. 4. In FIG. 4A, the distal end 34 of the catheter 28 is positioned against the myocardium 52 to be injected. The cartridge 32 is withdrawn within the distal end portion 34 of the catheter, and the plunger 28 is positioned towards the proximal end of the cartridge 32. On operation, the operating wire 40 moves towards the distal end 34 of the catheter, the cartridge 32 moves towards the distal end, with the plunger 38 remaining at the proximal end of the cartridge 32, so that the needle 36 penetrates the myocardium, thereby assuming the position shown in FIG. 4B. The next operation cannot cause any further movement of the cartridge 32 since it is already at the distal end 34 of the catheter 28 and in contact with the myocardium 52. Accordingly, this additional pressure causes movement of the plunger 38 within the cartridge 32 to expel therapeutic liquid from the cartridge through the needle 36 into the myocardium 52, as indicated in FIG. 4C.

By appropriate choice of length of needle 36 in the catheter of the present invention, penetration of the body organ wall such as the myocardium to an exactly predetermined extent can be arranged, so as to allow treatment of the myocardium 52 with therapeutic fluid without penetration thereof to the layers beyond. This makes the best possible use of the therapeutic fluid, and is particularly advantageous in the case of the use of very expensive therapeutic fluids such as DNA solutions for myocardial treatment. The apparatus can be arranged to deliver aliquots of fluid over volumetric range of 0.05–1 cc's. The apparatus can be arranged to deliver such an aliquot incrementally, by controlling the extent of movement of the plunger 38 within the cartridge 32. Thus there can be delivered a volume corresponding to the entire internal volume of the cartridge 32, or a carefully controlled portion thereof, depending upon the extent of movement of the plunger 38 therein.

Figure 5:
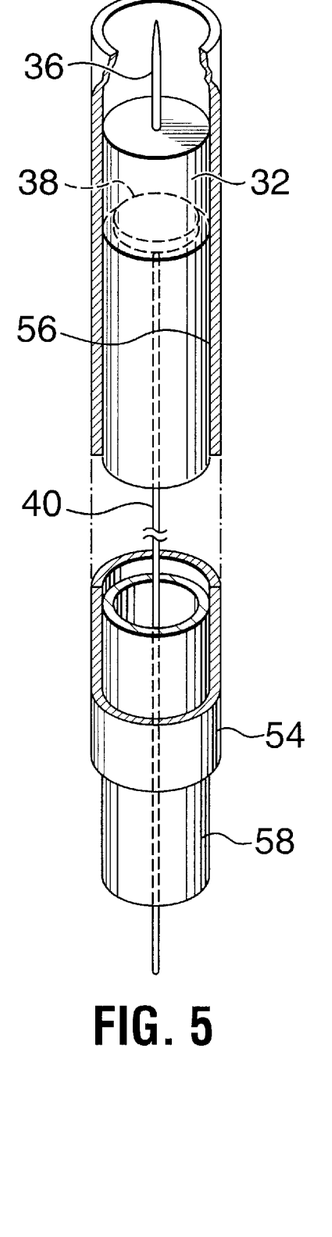
FIG. 5 is a diagrammatic detailed view of the distal end of a catheter according to a second embodiment of the invention.

FIG. 5 of the accompanying drawings shows the distal end portion of an alternative form of catheter according to the present invention, in which cartridge 32 is slidable within a guide catheter 54 and is mounted on the end of an injection catheter 58 which is moved by the operating means to position the cartridge 32 so that the needle 36 carried by it bears against and penetrates the myocardium. As in the previously described embodiment, the cartridge 32 contains a slidable plunger 38, which can be moved in response to movements of the operator wire 40 to expel liquid from the cartridge 32 through the needle 36, in the manner described with reference to FIG. 4.

Figure 6:
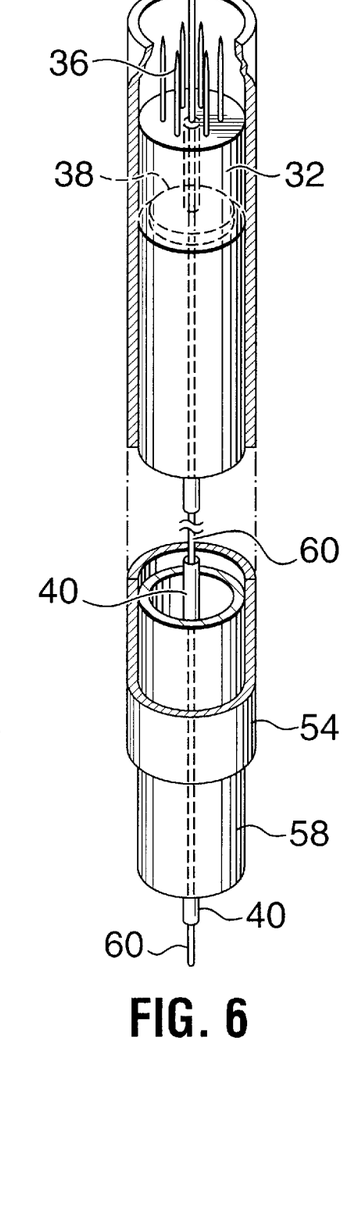
FIGS. 6 and 6A are diagrammatic detailed views of a third embodiment of the invention.
Figure 6A:
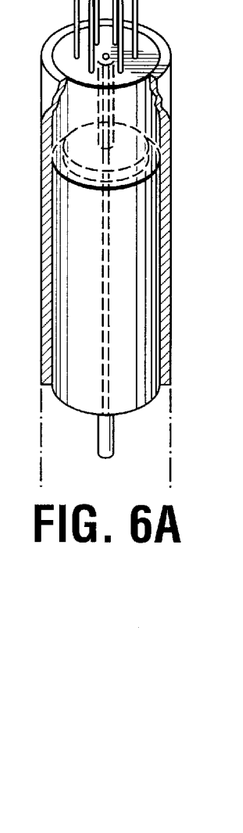

FIGS. 6 and 6a show a further alternative embodiment, similar to that shown in FIG. 5 but in which the cartridge 32 is equipped with a plurality of needles 36' for injecting into the myocardium, and which is additionally provided with a guide wire 60, extending through a centrally disposed tubular operating wire 40. The guide wire 60 extends beyond the distal end of the guide catheter 54, through cartridge 32, to lead the catheter into position against the myocardial wall 52. This facilitates access to parts of the myocardium where the catheter must make relatively sharp angled bends. When the guide wire 60 is in position against the myocardium, the operator can cause the guide catheter 54 and associated structure to slide along the guide wire 60 into position, and then the operator wire 40 can be operated to move first the cartridge 32 distally and then the plunger 38 distally within the cartridge 32, as indicated in FIG. 6A, and according to the steps illustrated in FIG. 4.

Figure 7A:
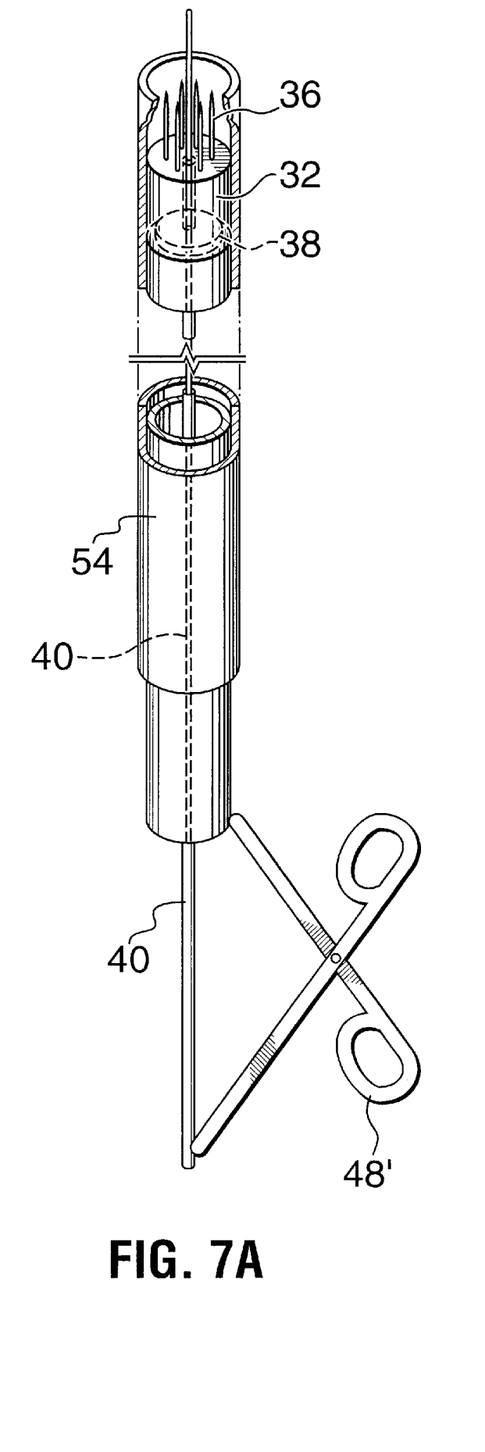
FIGS. 7A and 7B are diagrammatic detailed views of the distal end and operating means of a fourth embodiment of the invention.
Figure 7B:
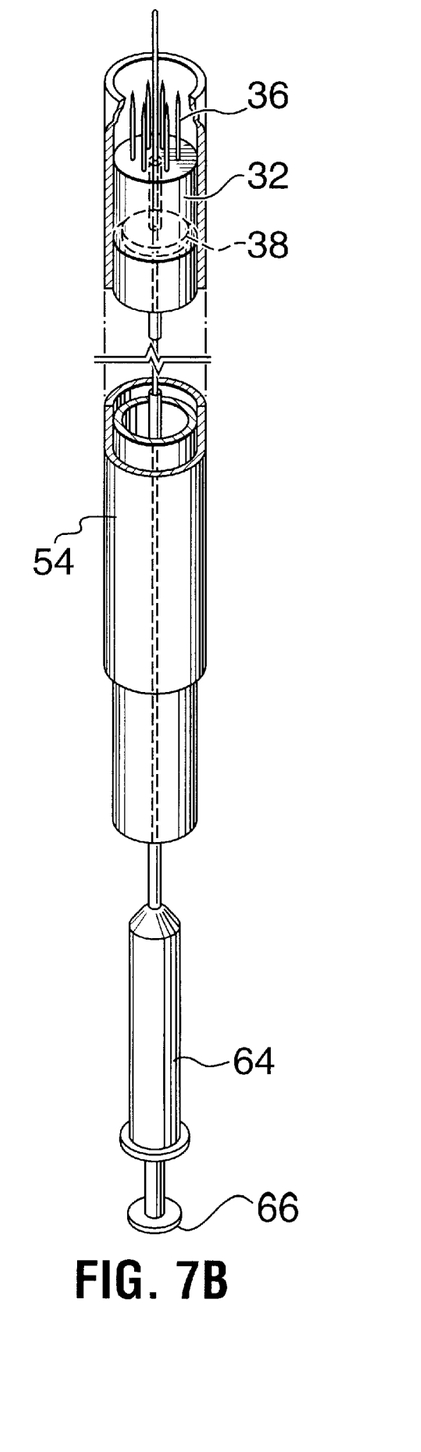

FIGS. 7A and 7B show alternative operating systems for use with catheters previously described. Both show the FIG. 6 embodiment. In FIG. 7A, the operating means for the plunger 38 and cartridge 32 is a mechanical scissors-style pivoted handle 48', one jaw of which is connected to operator wire 40 and the other to catheter 54, for relative movement thereof on pivoting the handle 62, through the operating stages shown in FIG. 4.

In FIG. 7B, the operator means is a hydraulic syringe 64 with a piston 66, the operation of which delivers hydraulic fluid under pressure through a conduit catheter, to move the cartridge 32 and plunger 38 through the operating stages shown in FIG. 4.

In alternative arrangements, the needle may be provided with a series of outlets, along the length thereof, as well as an outlet in its end tip. The needle may be designed in the form of a screw so that it can be used to penetrate and attach itself and the cartridge containing the drug directly to the myocardium. This arrangement secures the intramyocardial injection either through the end hole or through the end hole and side holes of the screw like needle.

In addition, a special type of guide wire may be used which contains a screw attached to its end to allow direct contact and attachment to the myocardial wall using the guide wire. Such a guide wire can be advanced through the guiding catheter and injecting catheter and the cartridge containing the drug, to be attached to the myocardial wall beyond the distal end of the catheter. After such attachment, direct intramuscular injection into the myocardial wall can be arranged.

Many other practical embodiments are encompassed by this invention, those described and illustrated being non-limiting examples. For example, in one alternative specific embodiment of the invention, not illustrated, the catheter comprises a flexible tube with at least one hollow injection needle mounted on and extending beyond its distal end, the needle or needles having an extent of protrusion of from about 1–8 mm. This length is chosen to be less than the thickness of myocardial wall. A guide wire extends through the length of the catheter, and through or around the needle, to lead the catheter into position against the selected portion of the myocardial wall. A mechanical operating means in the form of a syringe is provided at the proximal end, connected to an operating plunger at the distal end portion of the catheter. Thus, the portion of the catheter between the distal end thereof and the plunger provides the reservoir for therapeutic fluid carried by the catheter. Such an embodiment, omitting the guide wire, is described and illustrated below with reference to FIG. 9 of the accompanying drawings. In this embodiment, the catheter containing therapeutic fluid is led into position by the guide wire, further pushed by the operator until the needle(s) penetrate into the myocardial wall, and then the operating means is manually operated to expel the therapeutic fluid through the needle(s) into the myocardium. The operation is monitored on screen, as it is performed, as in the case of operation of the various other embodiments disclosed herein.

Figure 8A:
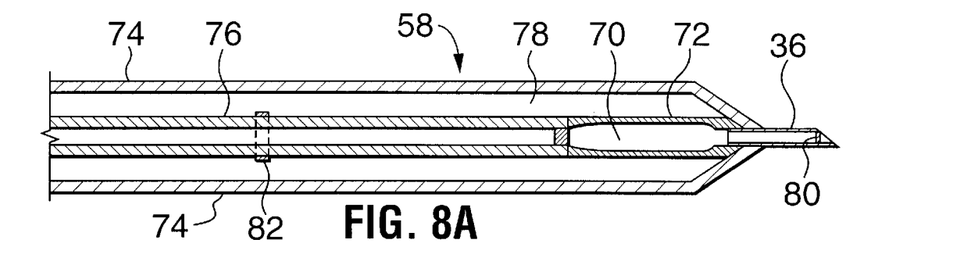
FIGS. 8A and 8B are diagrammatic, cross-sectional views of the distal end of a fifth embodiment of the invention, in two different operational positions.
Figure 8B:
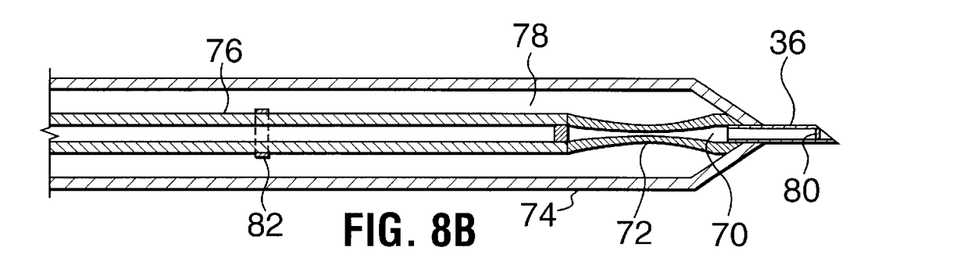

FIGS. 8A and 8B of the accompanying drawings diagrammatically illustrate a further embodiment of the invention. Instead of a cartridge, the reservoir for the therapeutic fluid to be injected comprises a chamber 70 at the distal end of the injection catheter 58, in fluid communication with and carrying an injection needle 36. The needle 36 extends beyond the distal end of the injection catheter 58 a predetermined distance appropriate for injection of fluid into the myocardium, as previously described. The chamber 70 is defined by compressible side walls 72 so that the chamber 70 can be compressed to expel the contents thereof through needle 36, as shown in FIG. 8B, by application of external fluid pressure to the side walls 72.

To accomplish this, the embodiment of FIGS. 8A and 8B includes an outer tube 74 of biocompatible material e.g. medical grade polyethylene, constituting a guiding catheter, and an inner tube 76 constituting an injection catheter and defining an annular space 78 between itself and the guide catheter. A source of fluid pressure e.g. compressed air can be connected to communicate with space 78, towards the proximal end of the catheter assembly, so as to pressurize the space 78 when required. The side walls 72 defining the chamber 70 are of softer material than that of the rest of the inner tube 76, although sealingly joined thereto, so that fluid pressure supplied to space 78 compresses chamber 70 to expel the contents thereof through needle 36 when required, without affecting inner tube 76. In practice, fluid for injection such as genetic material is introduced into the chamber 70 by means of a small injection needle through needle 36, so as to fill chamber 70. Then the injection catheter (inner tube 76) is introduced into the guide catheter tube 74, which may already be in place at the injection site. The injection catheter 76 is a sealing fit in the guide catheter 74. The injection catheter remains in the guide until it is positioned properly. The needle then is advanced out of the guide to penetrate the myocardial wall, or other chosen injection site, and injection fluid in predetermined measured amounts can be expelled through the needle 36 to the injection site at will, by supply of pressure to space 78. With the guide catheter 74 still in place, the injection catheter can be removed and reloaded.

Different relaxed sizes of chamber 70 can be adopted either by changing the diameter or by changing the length of the chamber, to accommodate different volumes of injection fluid.

The embodiment of FIGS. 8A and 8B also optionally includes a recording electrode 80 in the form of a ring around the distal, penetrating end of needle 36, and a reference electrode 82 disposed some 10–15 cm from the tip. With suitable, standard electrical circuitry arrangements, the recording electrode 80 can give the operator a visible or audible signal to indicate contact of the tip of needle 36 with the injection site or, alternatively, penetration thereof to the desired, predetermined depth, such as 2 mm, so that the operation of the injection procedure can commence. Similar recording and reference electrodes can be included on the other illustrated embodiments of the invention. Distance markers can also be included in appropriate locations.

Figure 9:
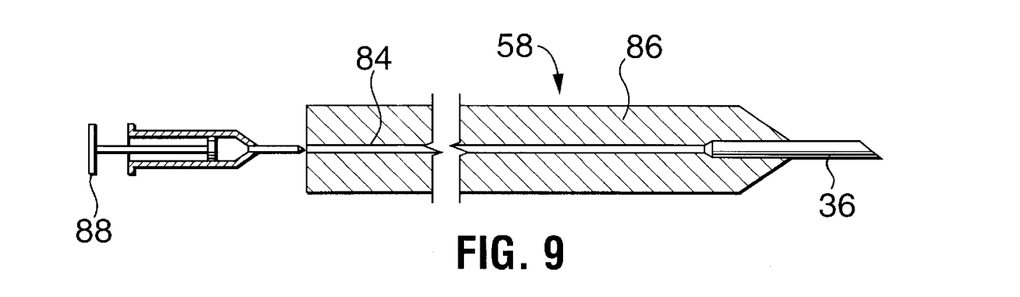
FIG. 9 is a diagrammatic cross-sectional view of a sixth embodiment of the invention.

FIG. 9 of the accompanying drawings illustrates a further embodiment of the invention. In this embodiment, the injection catheter 58 includes an injection lumen 84 of very small diameter, which serves as the reservoir for injection fluid and communicates with the injection needle 36 protruding from its distal end a short, predetermined distance such as 2 mm. The lumen 84 is defined by tubular side wall 86, e.g. of nylon, dimension 0.05"×0.010". This injection catheter 58 can be used with a guide catheter of the type shown on item 74 on FIGS. 8A and 8B. In operation, the lumen 84 is loaded with genetic injection fluid from its proximal end using a syringe 88, until a meniscus is formed at the distal needle 36. Depending on the amount of injection material required, the syringe 88 can be left in place on the proximal end, for additional injections. Then the injection catheter is introduced through a guide catheter, positioned at the location for injection, and the injection catheter is advanced 60 that the needle 36 penetrates the location, e.g. the myocardium. The exact amount of fluid can then be injected by operation of the syringe 88 on the proximal end. The catheter assembly can then be moved to the next area for injection, and the process repeated. A catheter of this design may have a length of 100 cm and a lumen diameter of 0.01 inch, giving an approximate capacity of 0.05 cc of injection fluid. With such a small volume lumen, very little injection fluid is lost.

We claim:

1. A catheter assembly comprising:
   an elongated flexible biocompatible tube constituting a guiding catheter and having a proximal end portion and a distal end portion;
   a reservoir adapted to contain treatment fluid and disposed in the distal end portion of the guiding catheter;

a guide wire extending through the reservoir to protrude beyond the distal end of the guiding catheter;

at least one needle adapted to protrude from the reservoir and beyond the distal end of the guiding catheter to a predetermined extent;

said at least one needle having a bore with an inlet communicating with the reservoir and an outlet disposed distally beyond the distal end of the guiding catheter;

operating means for delivering a predetermined quantity of treatment fluid from the reservoir through the needle outlet;

and an operating wire extending axially through the guiding catheter from the proximal end thereof to the reservoir, said operating wire connecting the reservoir to the operating means.

2. A catheter assembly of claim 1 wherein said operating means is operable to change the volume of said reservoir so as to expel the contents thereof through said at least one needle in predetermined quantity.

3. The catheter assembly of claim 2 wherein said reservoir comprises a cartridge having a distal end wall carrying said at least one needle and a proximal end wall constituted by a movable plunger connected to said operating means.

4. The catheter assembly of claim 3 wherein said cartridge is movable axially with respect to the guiding catheter in response to operation of the operating means.

5. The catheter assembly of claim 2 including an injection catheter disposed within and axially movable relative to said guiding catheter in response to operation of said operating means, said injection catheter incorporating the reservoir and means for changing the volume of the reservoir.

6. The catheter assembly of claim 5 wherein the reservoir comprises a generally cylindrical chamber having a distal end wall carrying said at least one injection needle, and a proximal end wall movable axially within the chamber in response to operation of the operating means to constitute the means for changing the volume of the reservoir.

7. The catheter assembly of claim 2 including an injection catheter disposed within the guiding catheter, said injection catheter having the reservoir formed therein and defined by deformable side walls, the operating means being operable to compress the reservoir to expel liquid contents thereof through the injection needle.

8. The catheter assembly of claim 7 wherein the operating means comprises a source of fluid pressure applicable to the exterior of the deformable side walls of the reservoir to effect compression thereof.

9. The catheter assembly of claim 1 wherein said operating wire is tubular.

10. The catheter assembly of claim 9 wherein the guide wire extends axially through the tubular operating wire.

11. The catheter assembly of claim 1 including an injection catheter disposed within the guiding catheter, said injection catheter having the reservoir formed therein as a narrow, axially extending lumen, connected at its proximal end to an operating means in the form of a syringe of liquid operable to apply liquid pressure to expel liquid from the lumen through the injection needle.

12. The catheter assembly of claim 1 wherein the guide wire extends through the needle.

13. A catheter assembly comprising:

an elongated flexible biocompatible tube constituting a guiding catheter and having a proximal end portion and a distal end portion;

an injection catheter disposed within the guiding catheter;

a reservoir adapted to contain treatment fluid and disposed within the injection catheter and at the distal end portion of the guiding catheter, said reservoir being defined by deformable side walls;

at least one needle adapted to protrude from the reservoir and beyond the distal end of the guiding catheter to a predetermined extent;

said at least one needle having a bore with an inlet communicating with the reservoir and an outlet disposed distally beyond the distal end of the guiding catheter;

operating means for delivering a predetermined quantity of treatment fluid from the reservoir through the needle outlet, said operating means comprising a source of fluid pressure applicable to the exterior of the deformable side walls of the reservoir to effect compression thereof for delivering said predetermined quantity of treatment fluid.

\* \* \* \* \*